US010933203B2

(12) United States Patent
Miller et al.

(10) Patent No.: US 10,933,203 B2
(45) Date of Patent: Mar. 2, 2021

(54) ADJUSTABLE MISTING ARRAYS

(71) Applicant: L'Oreal, Paris (FR)

(72) Inventors: Zane Bowman Allen Miller, Seattle, WA (US); Vincenzo Casasanta, III, Woodinville, WA (US); John Streeter, Redmond, WA (US)

(73) Assignee: L'Oreal, Paris (FR)

( * ) Notice: Subject to any disclaimer, the term of this patent is extended or adjusted under 35 U.S.C. 154(b) by 48 days.

(21) Appl. No.: 16/226,443

(22) Filed: Dec. 19, 2018

(65) Prior Publication Data

US 2020/0197629 A1 Jun. 25, 2020

(51) Int. Cl.
*A61M 11/00* (2006.01)
*B05B 17/00* (2006.01)
*A61M 15/00* (2006.01)

(52) U.S. Cl.
CPC ...... *A61M 11/005* (2013.01); *A61M 15/0001* (2014.02); *B05B 17/0638* (2013.01); *A61M 2210/04* (2013.01)

(58) Field of Classification Search
CPC ............ A61M 11/005; A61M 15/0001; A61M 15/0085; A61M 2210/04; B05B 1/14; B05B 1/16; B05B 1/169; B05B 1/18; B05B 1/185; A45D 34/04
USPC ........................................................ 239/102.2
See application file for complete search history.

(56) References Cited

U.S. PATENT DOCUMENTS 4,982,898 A 1/1991 Ballu
6,554,203 B2 * 4/2003 Hess ......................... A61L 9/14 239/102.2
7,841,335 B2 11/2010 Harrington et al.
2001/0029961 A1 * 10/2001 Laughlin ................ A61Q 19/04 132/200
2011/0289675 A1 * 12/2011 Dunki-Jacobs ......... E03C 1/057 4/668
2014/0151457 A1 * 6/2014 Wilkerson ............ H01L 41/042 239/4
2016/0001307 A1 * 1/2016 Schurle ................... B05B 1/185 239/468
2018/0169682 A1 * 6/2018 Miller ................... B05B 12/122
(Continued)

FOREIGN PATENT DOCUMENTS

EP 1952896 A1 8/2008
EP 2197313 B1 7/2011
(Continued)

OTHER PUBLICATIONS

International Search Report and Written Opinion, dated Apr. 15, 2020, issued in corresponding International Patent Application No. PCT/US2019/065245, filed Dec. 9, 2019, 18 pages.

*Primary Examiner* — Darren W Gorman
(74) *Attorney, Agent, or Firm* — Christensen O'Connor Johnson Kindness PLLC

(57) ABSTRACT

An adjustable misting system and method for treating a region of a biological surface is presented. In an embodiment, a reconfigurable misting nebulizer includes a first misting panel having a plurality of apertures configured to atomize a formulation, and a second misting panel coupled to the first misting panel having a plurality of apertures configured to atomize the formulation. In some embodiments, a relative position of the first misting panel with respect to the second misting panel is adjustable.

16 Claims, 7 Drawing Sheets

(56) References Cited

U.S. PATENT DOCUMENTS

| | | | |
|---|---|---|---|
| 2018/0177957 A1 | 6/2018 | Streeter et al. | |
| 2018/0178240 A1* | 6/2018 | Anzenberger | B05B 17/0646 |
| 2018/0236474 A1 | 8/2018 | Wang | |
| 2019/0217313 A1* | 7/2019 | Yang | B05B 1/16 |

FOREIGN PATENT DOCUMENTS

| | | | |
|---|---|---|---|
| JP | H07275751 A | 10/1995 | |
| KR | 20030021306 A | 3/2003 | |
| KR | 101990631 B1 | 6/2019 | |
| WO | 2009139069 A1 | 11/2009 | |
| WO | 2010069932 A1 | 6/2010 | |
| WO | 2011/010260 A1 | 1/2011 | |
| WO | WO-2011063726 A1 * | 6/2011 | B05B 1/1645 |

* cited by examiner

Figure 4:
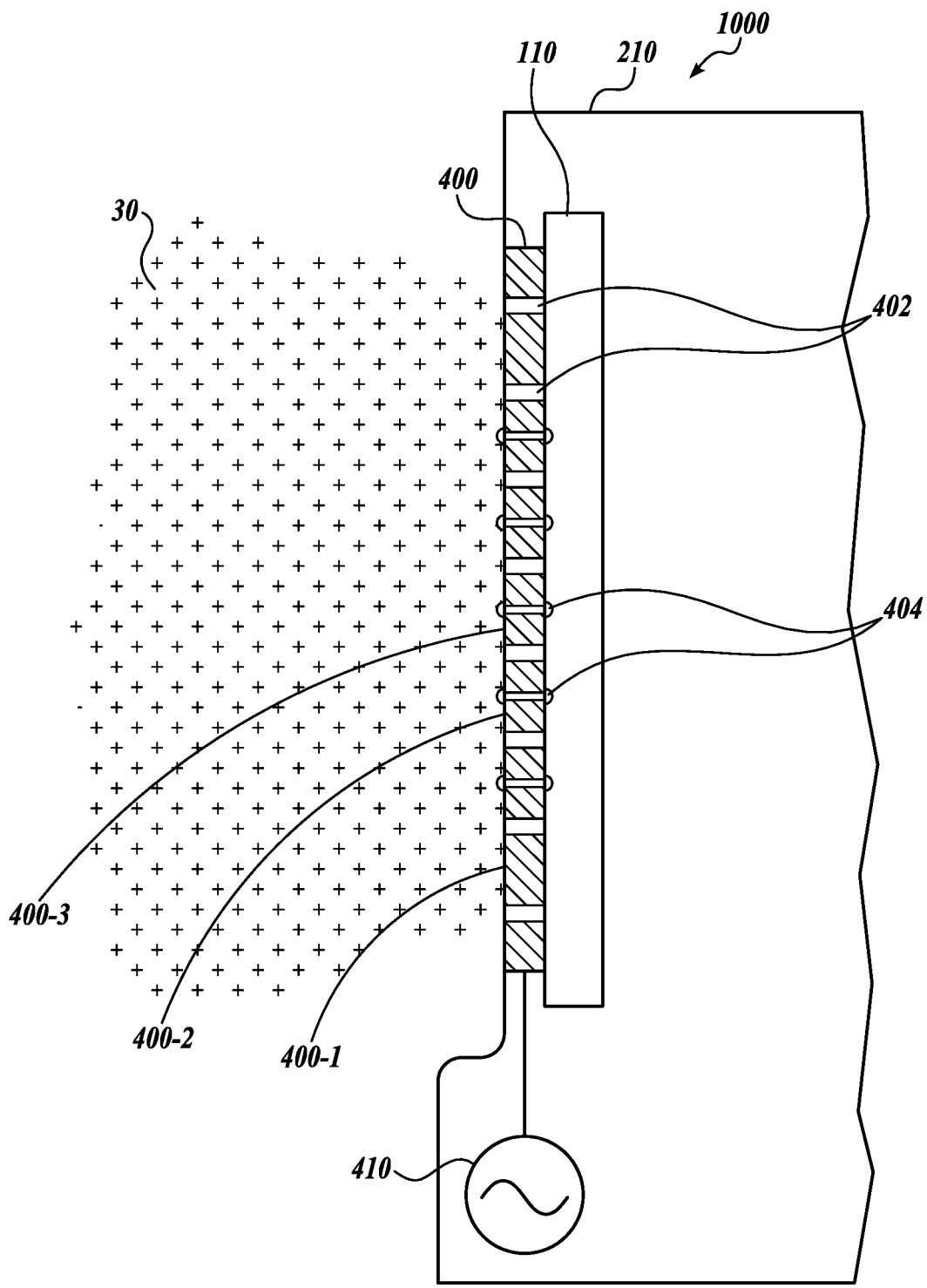

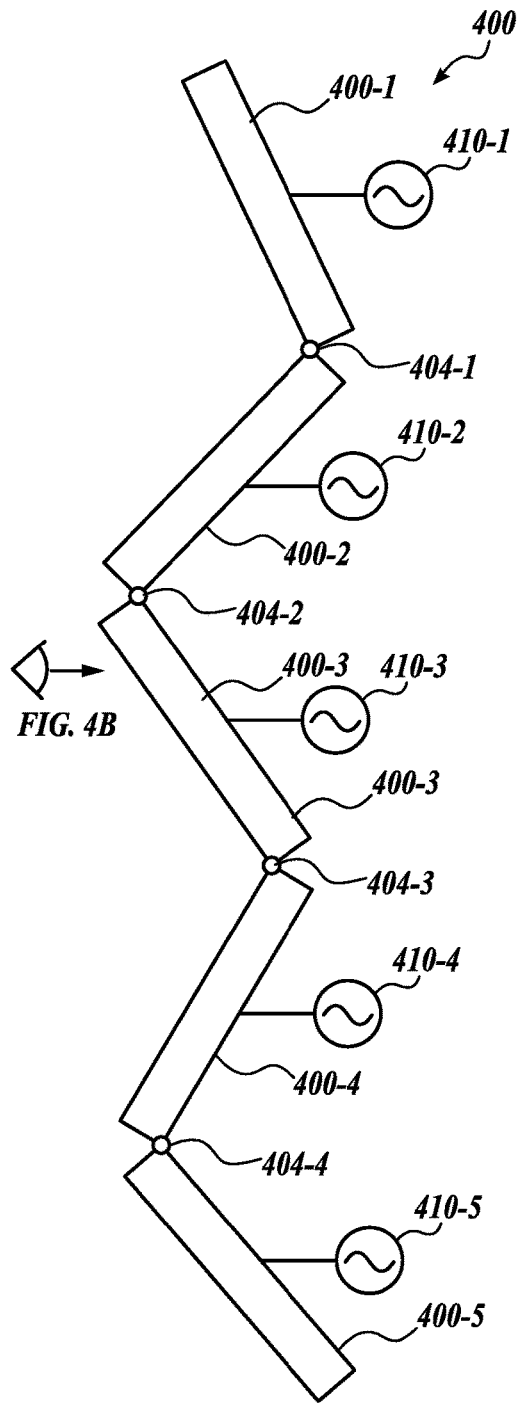
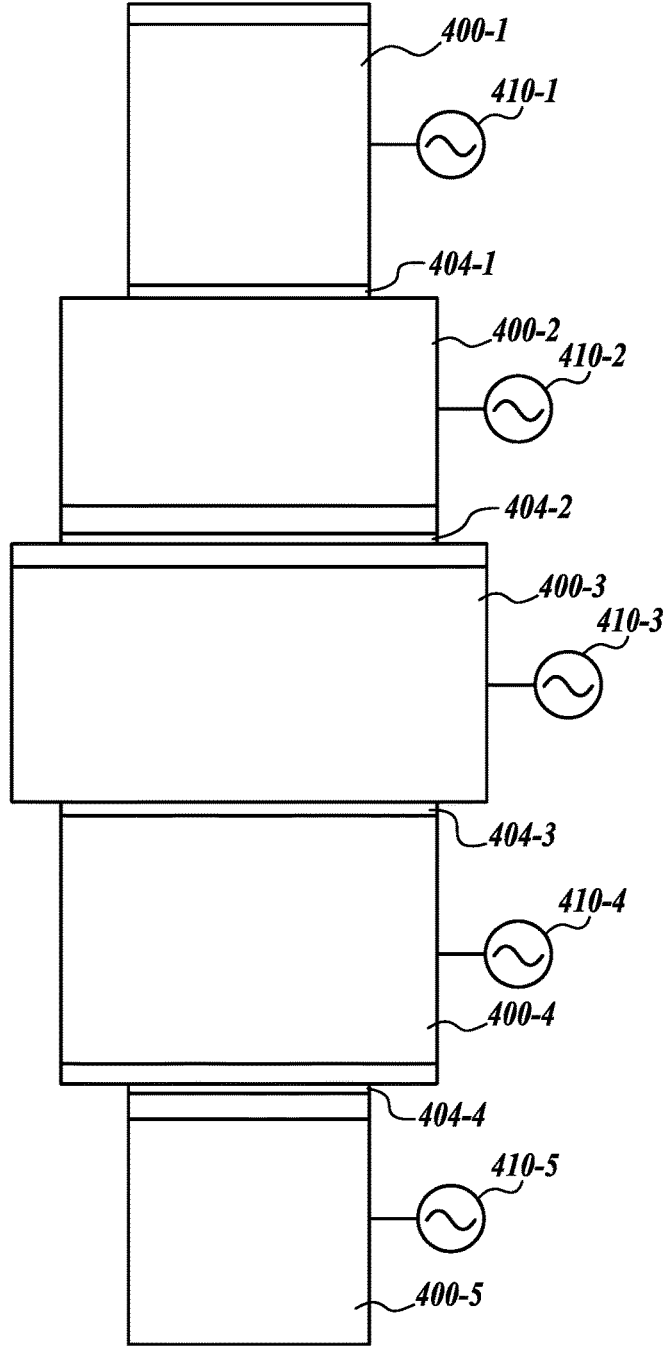
FIG. 4A  FIG. 4B

ADJUSTABLE MISTING ARRAYS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The inventive technology is directed to portable aerosol delivery devices (also referred to as "nebulizers"). The inventive technology may be implemented as a system, a method of operation, and/or a software application. In some embodiments, the nebulizers operate at ultrasonic frequencies to turn medicine or fragrance from a liquid phase into an aerosol mist. In operation, the liquid phase is subjected to high-frequency (e.g., ultrasonic) vibrations, therefore generating fine aerosol particles. In some applications, this fine mist is directed to user's face or other biological surface as a cosmetic or medical treatment. Compared to jet compressor nebulizers, ultrasonic nebulizers are relatively quiet, smaller in size and can quickly generate the aerosol mist.

In some embodiments, the aerosols are generated at a vibrating mesh (also referred to as "a vibrating transducer" or "a misting panel"). In general, mesh-based nebulizers generate aerosol particles of consistent size by atomizing the incoming liquid into aerosol particles as the incoming liquid flows through openings in the mesh. Because of their relatively low energy consumption, the mesh nebulizers can be portable units that are powered by a battery.

In some embodiments, the outer surface of a nebulizer may be adjustable. For example, the nebulizer may include multiple misting panels that are hingedly interconnected to form a shape that approximates the shape of user's face that is treated by the nebulizer, therefore improving the targeting of user's skin. When not in use, the misting panels may be removed and stored away as, for example, a stack of folded misting panels, therefore reducing the space needed by the nebulizer in its stored configuration. Transportability of such nebulizer is improved, because the nebulizer requires less space when not in use. In some embodiments, the nebulizer may include a single shapeable misting panel that can be folded into smaller space when not in use.

In some embodiments, individual misting panels of the nebulizer vibrate at different frequencies and/or amplitudes. In some embodiments, the nebulizer includes one or more proximity sensors that determine distance from the nebulizer to the target surface (e.g., user's face). Based on signals from the proximity sensor, the misting panels may be activated into vibration when a threshold distance is reached, thus not wasting the misting material or formulation when the nebulizer is too distant from the user for an efficient operation.

Figure 1:
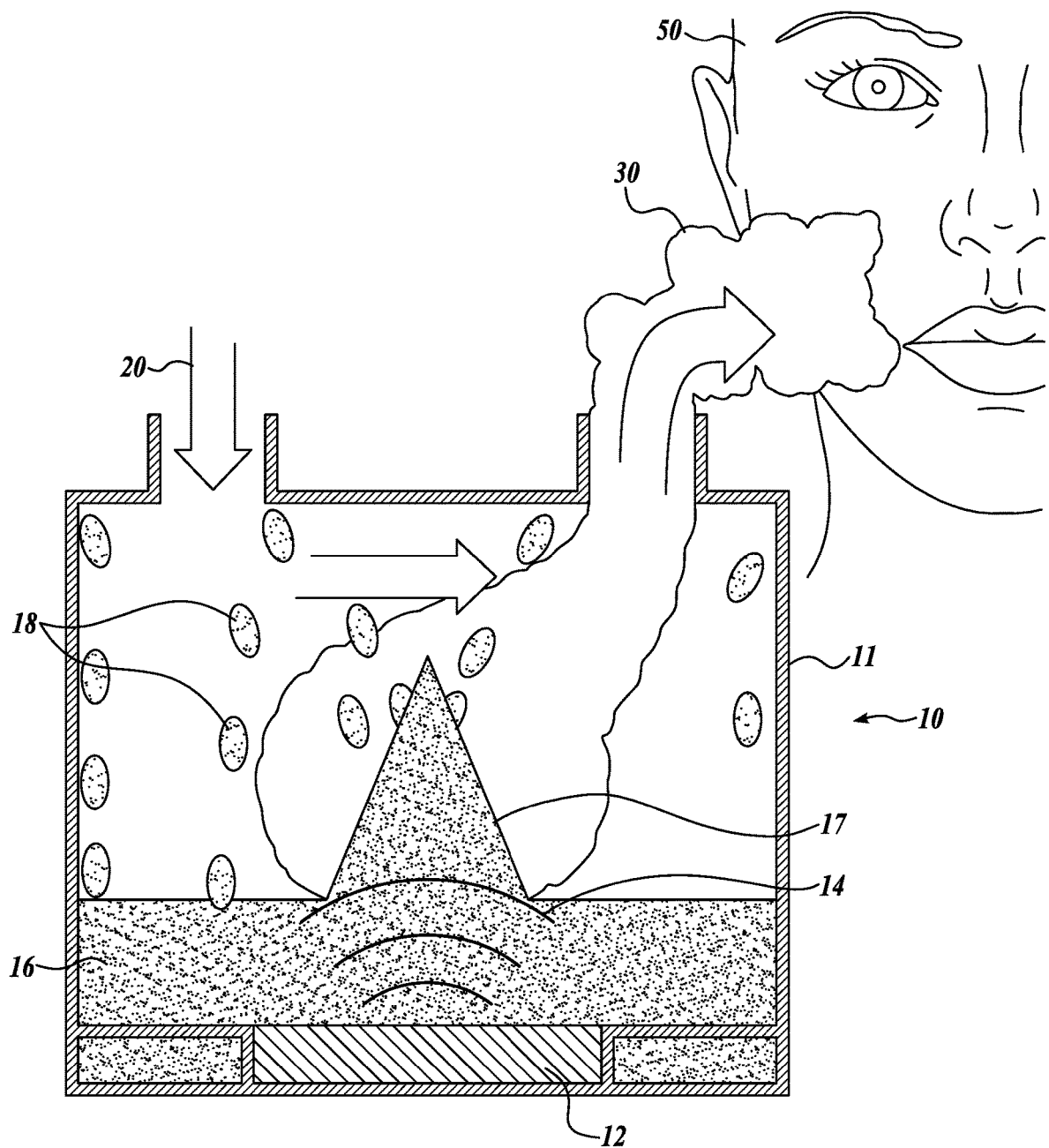

FIG. 1 is a partially schematic diagram of a nebulizer 10 in accordance with prior art. The nebulizer 10 holds misting material or formulation 16 (e.g., medication, water, fragrance, etc.) in a reservoir 11. In operation, a vibrating transducer 12 induces an acoustic field 14 into the misting material, therefore generating a liquid jet 17 and aerosol particles 18. Incoming air 20 carries the aerosol particles 18 as a respirable cloud 30 toward a user 50. However, the conventional nebulizer 10 is relatively large and inefficient, therefore lacking sufficient portability needed for, for example, travel.

Figure 2:
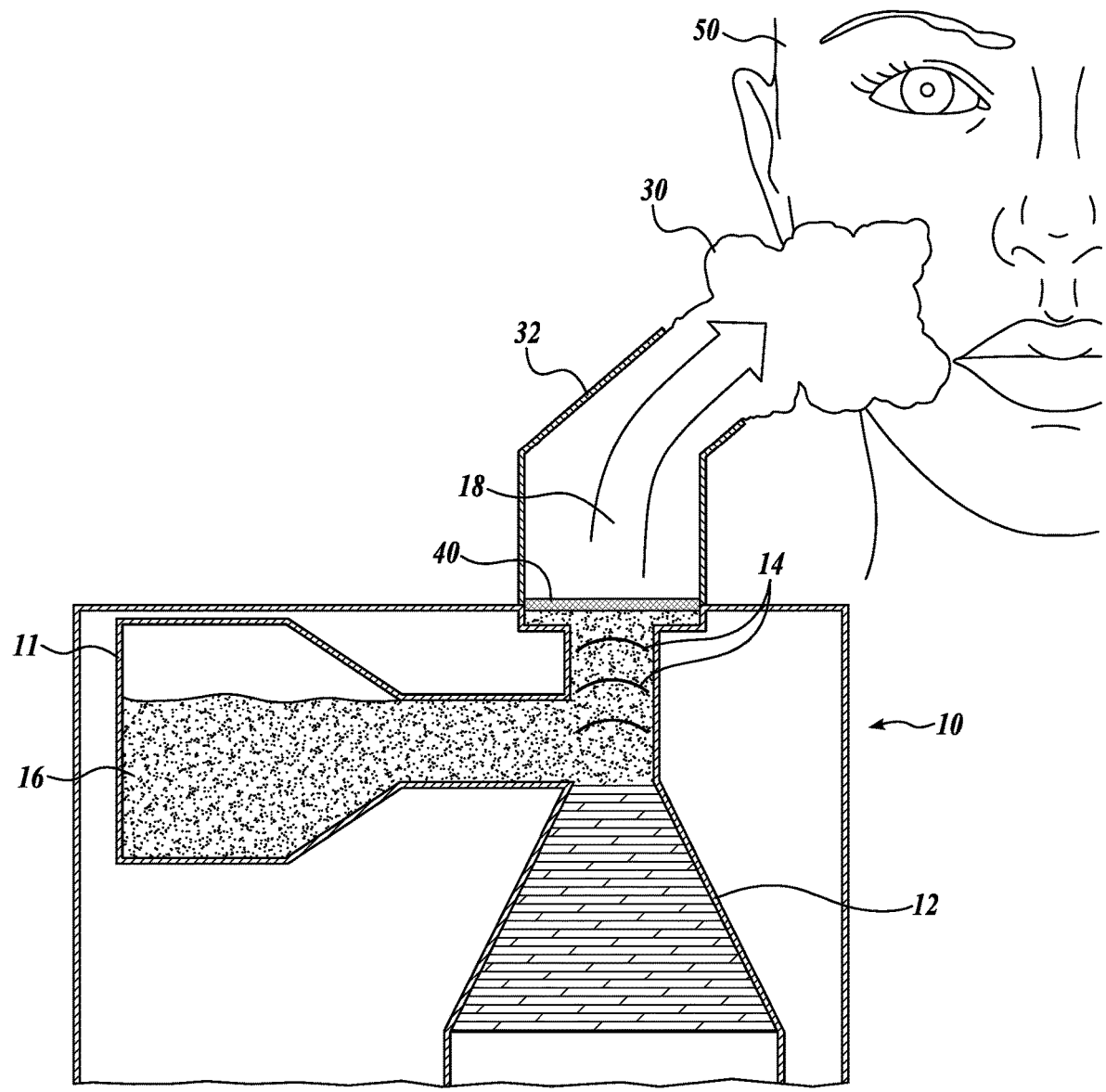
Figure 3:
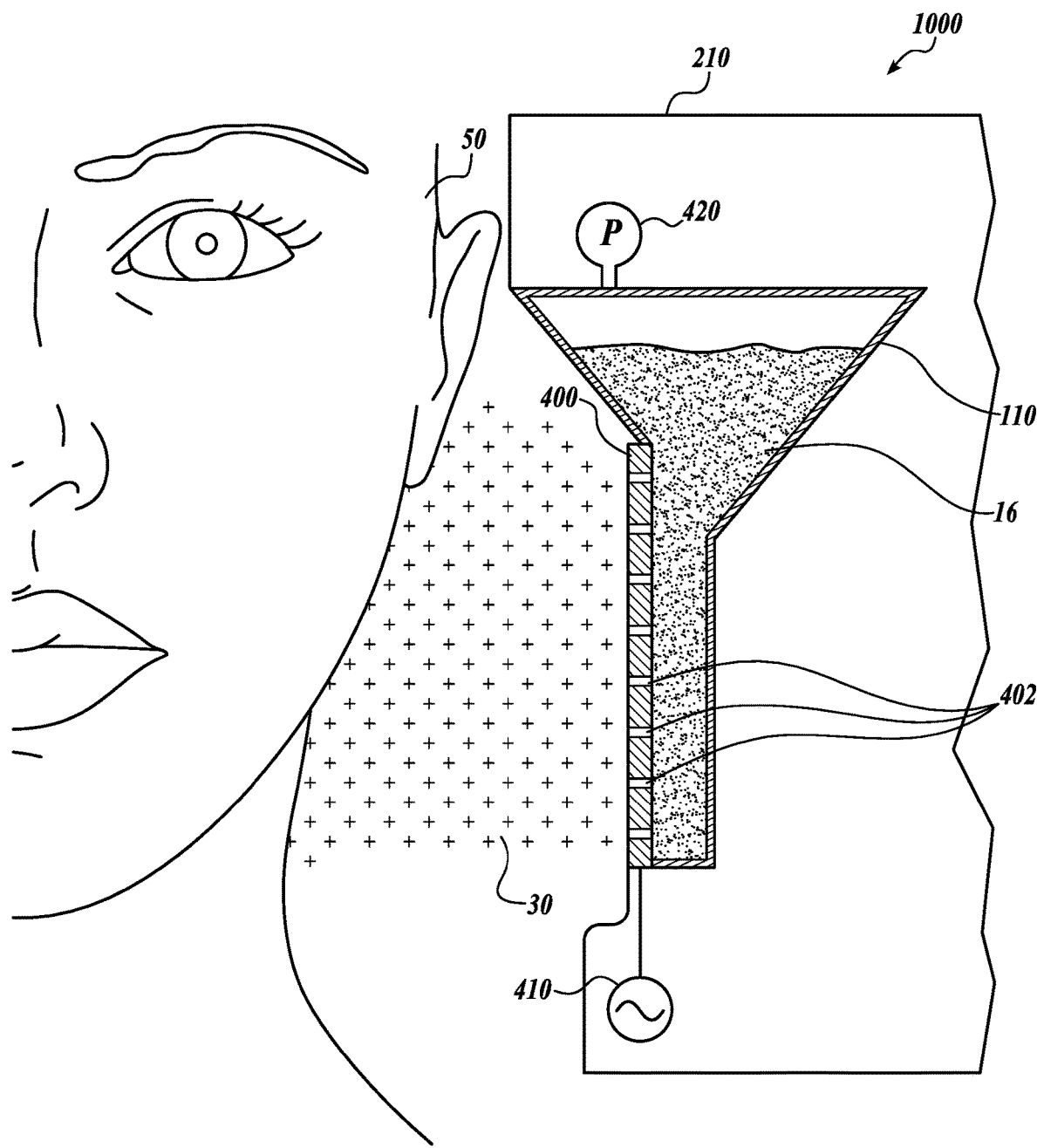

FIG. 2 is a partially schematic diagram of a nebulizer 10 in accordance with prior art. The nebulizer 10 includes the vibrating transducer 12 and a static wire mesh 40. The formulation 16 is contained inside a generally horizontal reservoir 11. In operation, the vibrating transducer 12 generates acoustic field 14 in the formulation 16. The static wire mesh 40 limits the outflow of the formulation 16 by retaining the liquid phase inside the reservoir 11, while allowing only the aerosol particles 18 to escape the reservoir. The aerosol particles 18 are next routed through an aerosol funnel 32 toward the user 50.

However, the conventional nebulizer 10 is still relatively large. For example, the illustrated conventional nebulizer 10 includes the vibrating transducer 12 for generating the acoustic field 14 and a separate static wire mesh 40 for preventing escape of the liquid phase from the nebulizer. Furthermore, the portability of the conventional nebulizer 10 is limited because of the aerosol funnel 32.

In an embodiment, a reconfigurable misting nebulizer includes: a first misting panel having a plurality of apertures configured to atomize a formulation; and a second misting panel coupled to the first misting panel. The second misting panel includes a plurality of apertures configured to atomize the formulation. A relative position of the first misting panel with respect to the second misting panel is adjustable.

In an aspect, the first misting panel and the second misting panel are hingedly coupled. The first misting panel and the second misting panel are coplanar when the nebulizer is in its operating configuration; and the first misting panel and the second misting panel are folded to face each other when the nebulizer is in its storage configuration.

In another aspect, the first misting panel has a first surface area and the second misting panel has a second surface area, and wherein the first surface area is different from the second surface area.

In an aspect, the first misting panel and the second misting panel belong to a first plurality of misting panels, and the nebulizer further includes a second plurality of misting panels hingedly coupled with corresponding misting panels of the first plurality of misting panels.

In another aspect, the first plurality of misting panels and the second plurality of misting panels form a surface contour that corresponds to an opposing surface contour of user's skin.

In another aspect, the first and second misting panels each comprise a plurality of openings configured for transporting the formulation from first sides of the individual misting panels to opposing second sides of the individual misting panels, where the second sides of the individual misting panels face user's skin.

In an aspect, the first and second misting panels are each fabricated from piezoelectric material. The nebulizer further includes a source of an alternating current (AC) connected to the first and second misting panels. The first and second misting panels are configured to vibrate in response to the AC.

In an aspect, the nebulizer also includes: a first source of alternating current (AC) connected to the first misting panel, where the first misting panel is fabricated from piezoelectric material configured to vibrate in response to the first source of AC; and a second source of AC connected to the second misting panel, where the second misting panel is fabricated from piezoelectric material configured to vibrate in response to the second source of AC. In another aspect, the first source of AC operates at a first frequency, the second source of AC operates at a second frequency, and the first frequency is different from the second frequency.

In an aspect, the nebulizer of also includes: a reservoir configured to hold the formulation in contact with the first and second misting panels; and a pump configured to pressurize the formulation inside the reservoir.

In another aspect, the nebulizer includes: a proximity detector configured to sense a distance between the nebulizer and a user; and a controller configured to activate the nebulizer upon receiving a proximity signal from the proximity detector.

In an embodiment, a reconfigurable misting nebulizer includes a foldable misting panel having a plurality of apertures configured to atomize a formulation. The foldable misting panel has a first configuration when the nebulizer is in an operating configuration, and has a second configuration when the nebulizer is in a storage configuration. In an aspect, the first configuration of the foldable misting panel is generally cylindrical or semispherical, and the second configuration of the foldable misting panel is generally spiral.

In another aspect, the first configuration of the foldable misting panel has a first shape that corresponds to an opposing shape of a surface of a user's skin.

In an aspect, the foldable misting panel is fabricated from piezoelectric material, the nebulizer further includes a source of an alternating current (AC) connected to the foldable misting panels, and the foldable misting panel is configured to vibrate in response to the AC.

In an aspect, a frequency of AC is within a range of ultrasound frequencies.

In an aspect, the nebulizer also includes: a reservoir configured to hold the formulation in contact with the foldable misting panel; and a pump configured to pressurize the formulation inside the reservoir.

In another aspect, the nebulizer also includes: a proximity detector configured to sense a distance between the nebulizer and a user; and a controller configured to activate the nebulizer upon receiving a proximity signal from the proximity detector.

In an aspect, the formulation in contact with the foldable misting panel is shapeable to approximate a shape of the foldable misting panel in the first configuration.

In another aspect, the formulation is selected from a group consisting of lotion, sunscreen, water, fragrance and makeup.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein:

FIG. 1 is a partially schematic diagram of a nebulizer in accordance with prior art;

FIG. 2 is a partially schematic diagram of a nebulizer in accordance with prior art;

FIG. 3 is a partially schematic diagram of a nebulizer in accordance with the present technology;

FIG. 4 is a partially schematic diagram of a nebulizer in accordance with the present technology;

FIGS. 4A and 4B are respectively side and front views of misting panels in accordance with the present technology;

FIG. 5 is a partially schematic diagram of a nebulizer in accordance with the present technology;

FIG. 5A is a schematic diagram of a misting panel in accordance with the present technology; and FIG. 6 is a partially schematic diagram of a nebulizer in accordance with the present technology.

DETAILED DESCRIPTION

The following description provides several examples of reconfigurable misting nebulizers, such as systems used to apply an atomized formulation to a skin portion.

FIG. 3 is a partially schematic diagram of a nebulizer 1000 in accordance with the present technology. In some embodiments, a reservoir or a cartridge 110 contains a misting material or formulation 16 (e.g., liquid lotion, sunscreen, water, fragrance, makeup, etc.). In different embodiments, the formulation 16 may be a liquid or gel. The cartridge 110 may be held against a misting panel 400 by mechanical means (e.g., clips, fasteners, elastomer, etc.). The cartridge 110 may be partially porous or open on the side that faces the misting panel 400, thus allowing the formulation 16 to flow through the openings 402 of the misting panel 400.

In different embodiments, the atomization of the formulation 16 is achieved by different modalities. For example, in some embodiments, the cartridge 110 may be pressurized by a source of pressure 420 (e.g., a pump, a source of compressed air, a miniature compressor, etc.). The elevated pressure inside the cartridge 110 drives the formulation 16 through the openings 402 of the misting panel 400, thus generating aerosol particles 30 in the direction of user 50.

In other embodiments, the misting panel 400 is energized by an energy source 410. For example, the misting panel 400 may be manufactured of piezoelectric material that expands and constricts when energized by alternate current (AC). As a result, the misting panel 400 vibrates at the frequency of AC, drawing the formulation 16 into the openings 402 as a liquid or gel, and ejecting aerosol particles 30 out of the openings 402. The magnitude and frequency of AC may at least in part define size and flow rate of aerosol particles 30. In some embodiments, frequency of the AC may be within an audible (sonic) or ultrasonic range.

In some embodiments, multiple modalities for generating aerosol are used. For example, the cartridge 110 may be pressurized while the vibrating misting panel 400 is energized through the AC source 410.

In some embodiments, the openings 402 have different sizes in different regions of the misting panel 400. A user may select an operating region of the misting panel 400 by, for example, occluding the non-used portions of the misting panel 400, thus controlling, for example, a flow rate of the formulation 16.

In some embodiments, the openings 402 are formed at different angles with respect to the plane of the misting panel 400. As a result, the flow of the aerosol 30 may be directed to different portions of skin of the user 50.

FIG. 4 is a partially schematic diagram of a nebulizer 1000 in accordance with the present technology. The illustrated nebulizer includes a cartridge 110 inside a nebulizer housing 210. The cartridge 110 delivers the formulation to a misting panel 400. In the illustrated embodiment, the misting panel 400 is energized by the AC energy source 410, but in different embodiments other modes of atomizing the formulation are possible.

The nebulizer 1000 includes several misting panels 400-1, 400-2, 400-3, etc. (collectively, "misting array" or "adjustable misting array"). In some embodiments, the misting panels are hingedly interconnected using joining elements 404. As a result, the outer surface of the group of misting panels may be configurable into a shape that, for example, corresponds to the shape of the opposing skin surface of the user. Some embodiments of the interconnected misting panels 400-*i* are described with reference to FIGS. 4A and 4B below.

FIGS. 4A and 4B are respectively side and front views of the misting panels in accordance with the present technology. FIG. 4A illustrates the misting panels 400-*i* (adjustable misting array) that are interconnected through the joining elements 404-*i*. In different embodiments, the joining elements 404-*i* may be hinges, magnetic elements, sleeves configured to hold edges of the misting panels, etc. Because the misting panels 400-*i* can be arranged in different relative positions with respect to each other, the collective outer surface of the misting panels may be constructed to at least partially follow the opposing surface of the user's skin. In at least some embodiments, when the nebulizer is not in operation, the misting panels 400-*i* may be removed and folded to require less space than the operating position of the misting panels. As a result, the portability of the nebulizer may be increased. In some embodiments, the individual misting panels 400-*i* are powered by their individual energy sources 410, but in different embodiments the individual misting panels 400-*i* may be powered by a common energy source 410.

FIG. 4B is a side view of the misting panels 400-*i* shown in FIG. 4A. Illustrated misting panels 400-*i* have different lengths and widths, therefore further enabling different shapes of the outer surface contour of the nebulizer. In some embodiments, the individual misting panels 400-*i* may be curved, therefore adding to the variety and complexity of the shapes that the outer surface contour of the misting panels can have when, for example, conforming to the corresponding surface contour of user's face.

Figure 5:
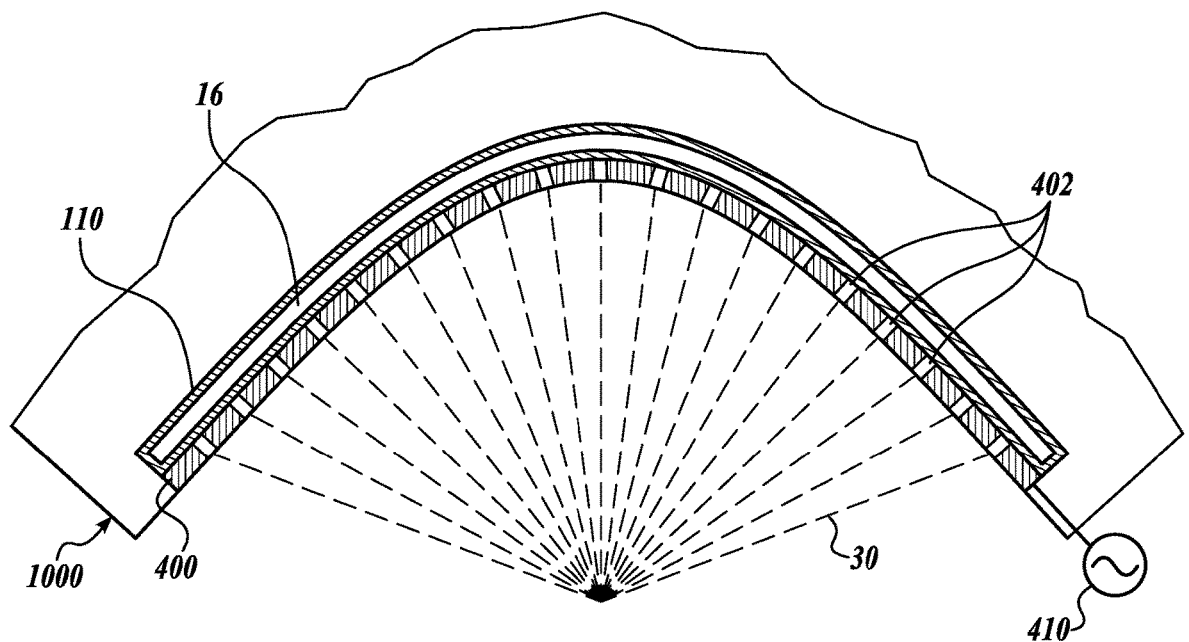

FIG. 5 is a partially schematic diagram of a nebulizer 1000 in accordance with the present technology. In some embodiments, the nebulizer 1000 includes a curved misting panel 400. For example, the openings 400 in the misting panel 400 may be directed toward a focal area or a focal point at the user's face. Therefore, aerosol particles 30 may better target a particular region of the user's skin.

Figure 5A:
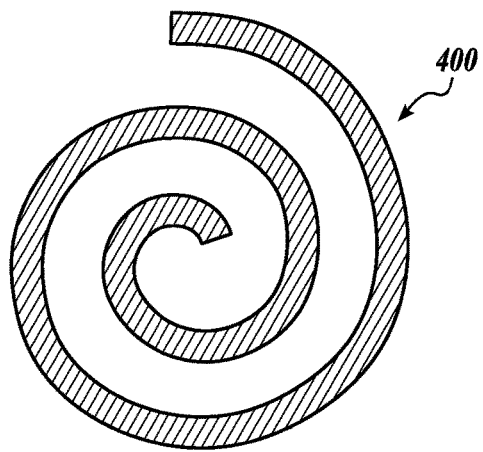

FIG. 5A is a schematic diagram of the misting panel 400 in accordance with the present technology. The illustrated misting panel 400 is arranged in a spiral shape when not in use. As a result, storage space required for the misting panel 400 is reduced and the portability of the nebulizer is improved.

Figure 6:
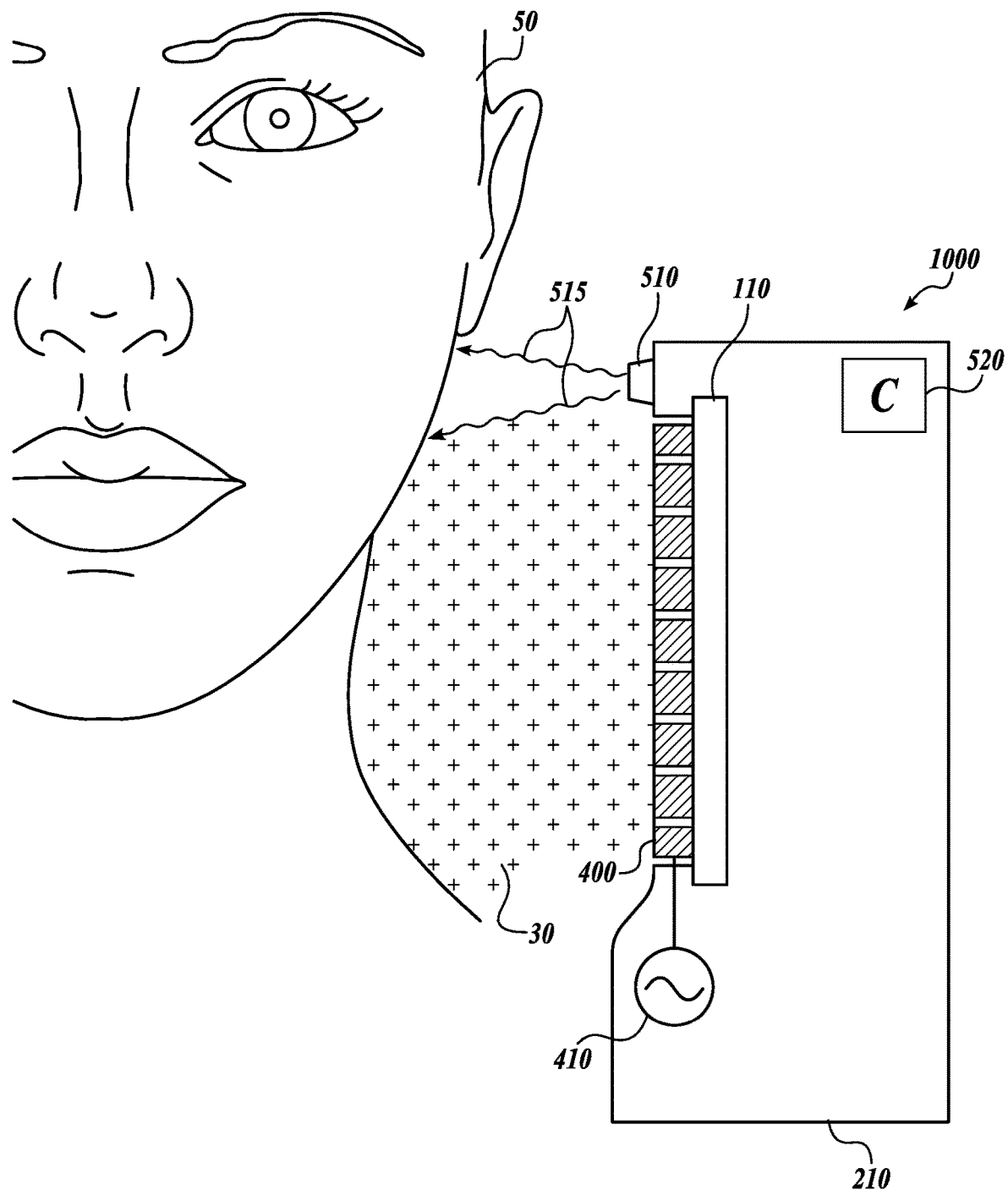

FIG. 6 is a partially schematic diagram of a nebulizer 1000 in accordance with the present technology. The illustrated nebulizer 1000 includes one or more proximity sensors 510. In operation, the proximity sensor 510 emits proximity signals 515 (e.g., ultrasound signal, light signal, etc.) toward the user 50 to estimate a distance between the nebulizer and the user. The proximity signals 515 may be received and processed by a controller 520. In some embodiments, the controller 520 activates the misting panel 400 when a pre-determined distance threshold is reached, therefore keeping the misting panel 400 off when the nebulizer 1000 is too far away from the user 50. As a result, the formulation may be used more effectively and economically.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, application specific integrated circuit (ASIC), controller or data processor that is specifically programmed, configured or constructed to perform one or more of the computer-executable instructions described above. Of course, any logic or algorithm described herein can be implemented in software or hardware, or a combination of software and hardware.

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Where methods are described, the methods may include more, fewer, or other steps. Additionally, steps may be performed in any suitable order. Accordingly, the disclosure can encompass other embodiments not expressly shown or described herein.

For the purposes of the present disclosure, lists of two or more elements of the form, for example, "at least one of A, B, and C," is intended to mean (A), (B), (C), (A and B), (A and C), (B and C), or (A, B, and C), and further includes all similar permutations when any other quantity of elements is listed.

We claim:

1. A reconfigurable misting nebulizer, comprising:
a first misting panel having a plurality of openings configured to atomize a formulation;
a second misting panel coupled to the first misting panel, the second misting panel having a plurality of openings configured to atomize the formulation; and
a source of an alternating current (AC) connected to the first and second misting panels,
wherein a relative position of the first misting panel with respect to the second misting panel is adjustable, wherein the first and second misting panels are each fabricated from piezoelectric material, and wherein the first and second misting panels are configured to vibrate in response to the AC,
wherein the first misting panel and the second misting panel are hingedly coupled, and wherein:
the first misting panel and the second misting panel are coplanar when the nebulizer is in its operating configuration; and
the first misting panel and the second misting panel are folded to face each other when the nebulizer is in its storage configuration.

2. The nebulizer of claim 1, wherein the first misting panel has a first surface area and the second misting panel has a second surface area, and wherein the first surface area is different from the second surface area.

3. The nebulizer of claim 1, wherein the first misting panel and the second misting panel belong to a first plurality of misting panels, the nebulizer further comprising a second plurality of misting panels hingedly coupled with corresponding misting panels of the first plurality of misting panels.

4. The nebulizer of claim 3, wherein the first plurality of misting panels and the second plurality of misting panels form a surface contour that corresponds to an opposing surface contour of user's skin.

5. The nebulizer of claim 1, wherein the plurality of openings of the first misting panel and of the second misting panel are configured for transporting the formulation from first sides of the individual misting panels to opposing second sides of the individual misting panels, and wherein the second sides of the individual misting panels face user's skin.

6. The nebulizer of claim 1, further comprising:
a reservoir configured to hold the formulation in contact with the first and second misting panels; and
a pump configured to pressurize the formulation inside the reservoir.

7. The nebulizer of claim 1, further comprising:
a proximity detector configured to sense a distance between the nebulizer and a user; and
a controller configured to activate the nebulizer upon receiving a proximity signal from the proximity detector.

8. A reconfigurable misting nebulizer, comprising:
a first misting panel having a plurality of openings configured to atomize a formulation;
a second misting panel hingedly coupled to the first misting panel, the second misting panel having a plurality of openings configured to atomize the formulation, wherein:
the first misting panel and the second misting panel are coplanar when the nebulizer is in its operating configuration, and
the first misting panel and the second misting panel are folded to face each other when the nebulizer is in its storage configuration;
a first source of alternating current (AC) connected to the first misting panel, wherein the first misting panel is fabricated from piezoelectric material configured to vibrate in response to the first source of AC; and
a second source of AC connected to the second misting panel, wherein the second misting panel is fabricated from piezoelectric material configured to vibrate in response to the second source of AC,
wherein a relative position of the first misting panel with respect to the second misting panel is adjustable.

9. The nebulizer of claim 8, wherein the first source of AC operates at a first frequency, wherein the second source of AC operates at a second frequency, and wherein the first frequency is different from the second frequency.

10. A reconfigurable misting nebulizer, comprising:
a foldable misting panel having a plurality of openings configured to atomize a formulation, wherein the foldable misting panel has a first configuration when the nebulizer is in an operating configuration, and wherein the foldable misting panel has a second configuration when the nebulizer is in a storage configuration, wherein the first configuration of the foldable misting panel is generally cylindrical or semispherical, and wherein the second configuration of the foldable misting panel is generally spiral.

11. The nebulizer of claim 10, wherein the first configuration of the foldable misting panel has a first shape that corresponds to an opposing shape of a surface of a user's skin.

12. The nebulizer of claim 10, wherein the foldable misting panel is fabricated from piezoelectric material, the nebulizer further comprising a source of an alternating current (AC) connected to the foldable misting panel, and wherein the foldable misting panel is configured to vibrate in response to the AC.

13. The nebulizer of claim 12, wherein a frequency of AC is within a range of ultrasound frequencies.

14. The nebulizer of claim 10, further comprising:
a reservoir configured to hold the formulation in contact with the foldable misting panel; and
a pump configured to pressurize the formulation inside the reservoir.

15. The nebulizer of claim 10, further comprising:
a proximity detector configured to sense a distance between the nebulizer and a user; and
a controller configured to activate the nebulizer upon receiving a proximity signal from the proximity detector.

16. The nebulizer of claim 10, wherein the formulation is selected from a group consisting of lotion, sunscreen, water, fragrance and makeup.

* * * * *